US005899883A

United States Patent [19]
Chern et al.

[11] Patent Number: 5,899,883
[45] Date of Patent: May 4, 1999

[54] SAFETY SYRINGE

[75] Inventors: Jino-Shing Chern; Yuh Lin Harn, both of Taipei, Taiwan

[73] Assignee: Jinq Shing Chern

[21] Appl. No.: 09/111,517

[22] Filed: Jul. 8, 1998

[51] Int. Cl.$^6$ ............................... A61M 5/00; A61M 5/32
[52] U.S. Cl. ........................ 604/110; 604/195; 604/240
[58] Field of Search ..................................... 604/110, 187, 604/188, 192, 194–196, 218, 226, 236, 238, 240, 241, 263

[56] References Cited

U.S. PATENT DOCUMENTS

| | | | |
|---|---|---|---|
| 5,069,225 | 12/1991 | Okamura | 604/240 |
| 5,242,401 | 9/1993 | Colsky | 604/198 |
| 5,533,980 | 7/1996 | Sweeney et al. | 604/110 |
| 5,667,494 | 9/1997 | Van Den Haak | 604/110 |
| 5,697,907 | 12/1997 | Gaba | 604/110 |

FOREIGN PATENT DOCUMENTS

| | | | |
|---|---|---|---|
| 2210270 | 6/1989 | United Kingdom | 604/110 |
| 2266667 | 11/1993 | United Kingdom | 604/110 |
| WO 92/05821 | 4/1992 | WIPO | 604/110 |

*Primary Examiner*—Wynn Wood Coggins
*Assistant Examiner*—Sharon Finkel
*Attorney, Agent, or Firm*—A & J

[57] ABSTRACT

A safety syringe includes a tubular barrel having a bottom formed with an opening and a top formed with a neck portion, a plunger configured to be slidably fitted in the barrel and provided with a rubber piston 21 at an inner end thereof and a thumb plate 22 at an outer end thereof, a cylindrical connector having a bottom formed with a flange, a first annular projection above the flange, and a second annular projection above the first annular projection, and a needle including a tubular pin and a conical base at a lower end of the tubular pin, whereby the risk of contracting dieseases from accidental sticks with dirty needles can be totally avoided.

1 Claim, 7 Drawing Sheets

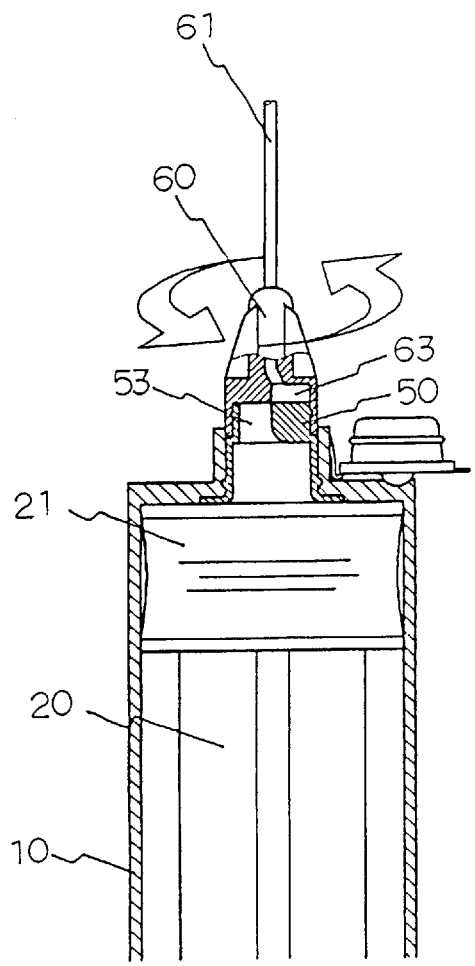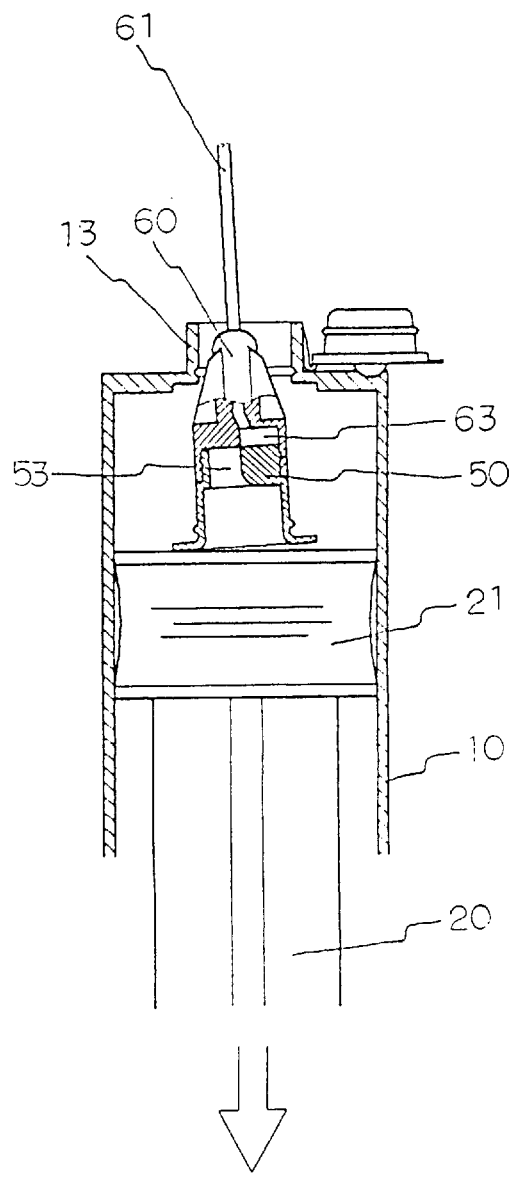
FIG. 7 A
FIG. 7 B

SAFETY SYRINGE

BACKGROUND OF THE INVENTION

1. Field of the Invention

This invention is related to a safety syringe and in particular to one for avoiding accidental sticks.

2. Description of the Prior Art

It has been found that the risk of contracting diseases from accidental sticks with dirty needles is a potentailly deadly hazard for medical professionals. As shown in FIGS. 1 and 2, the conventional syringe includes a barrel 10, a plunger 20, a needle 30 and a cover 40. The barrel 10 is a tubular member having an opening at the lower end so that the plunger 20 can be fitted into the barrel 10. The upper end of the barrel 10 is formed with a neck 12. The plunger 20 has a cross-shaped section and is provided with a rubber piston 21 at the upper end and a thumb plate 22 at the lower end. The needle 30 is a tubular member having a pointed end with a small opening 31. The other end of the needle 30 has an annular portion 32 dimensioned to fit over the neck 12 of the barrel 10. The cover 40 is used for enclosing the needle 30 when the syringe is not in use. However, the cover 40 is easily disengaged from the needle 30 thereby often causing the risk of contracting dieseases from accidental sticks.

Therefore, it is an object of the present invention to provide a safety syringe which can obviate and mitigate the above-mentioned drawbacks.

SUMMARY OF THE INVENTION

This invention is related to an improved safety syringe.

It is the primary object of the present invention to provide a safety syringe which can avoid accidental sticks.

It is another object of the present invention to provide a safety syringe which is easy to use.

It is still another object of the present invention to provide a safety syringe which is low in cost.

It is still another object of the present invention to provide a safety syringe which is simple in construction.

It is a further object of the present invention to provide a safety syringe which is fit for practical use.

The foregoing objects and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

BRIEF DESCRIPTION OF THE DRAWINGS

FIG. 3A is an enlarged fragmentary view of FIG. 3;

FIG. 3B is another enlarged fragmentary view of FIG. 3;

FIGS. 7A and 7B are sectional views illustrating how to draw the needle inside the barrel.

DETAILED DESCRIPTION OF THE PREFERRED EMBODIMENT

Figure 1:
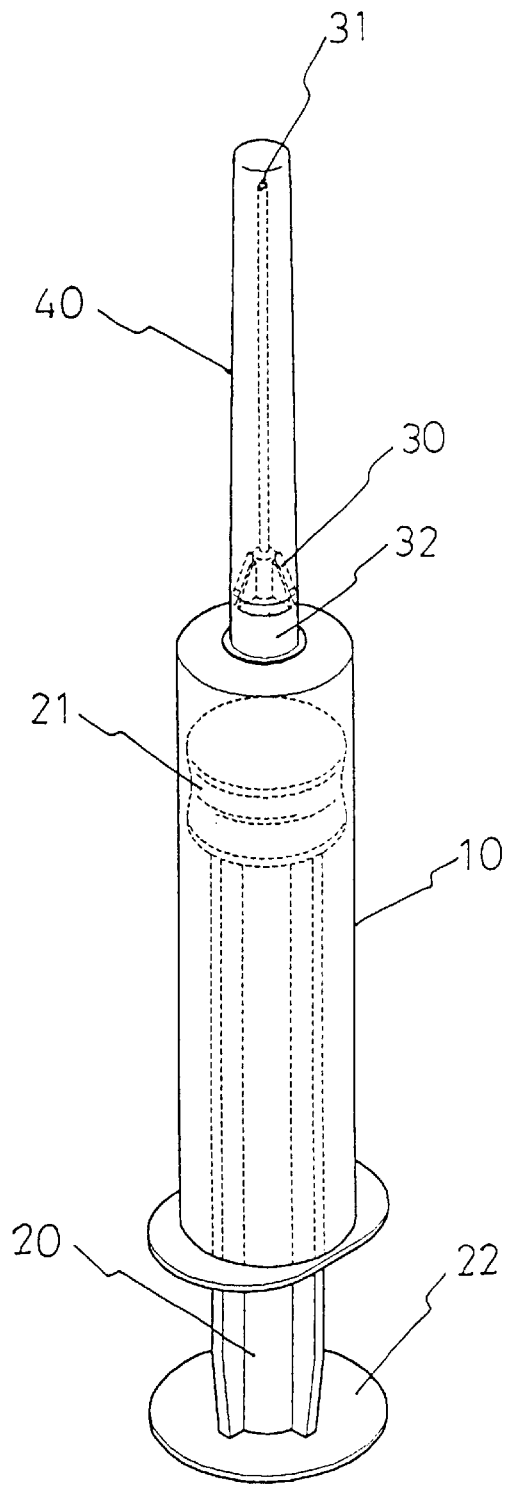
FIG. 1 is a perspective view of a prior art syringe.
Figure 2:
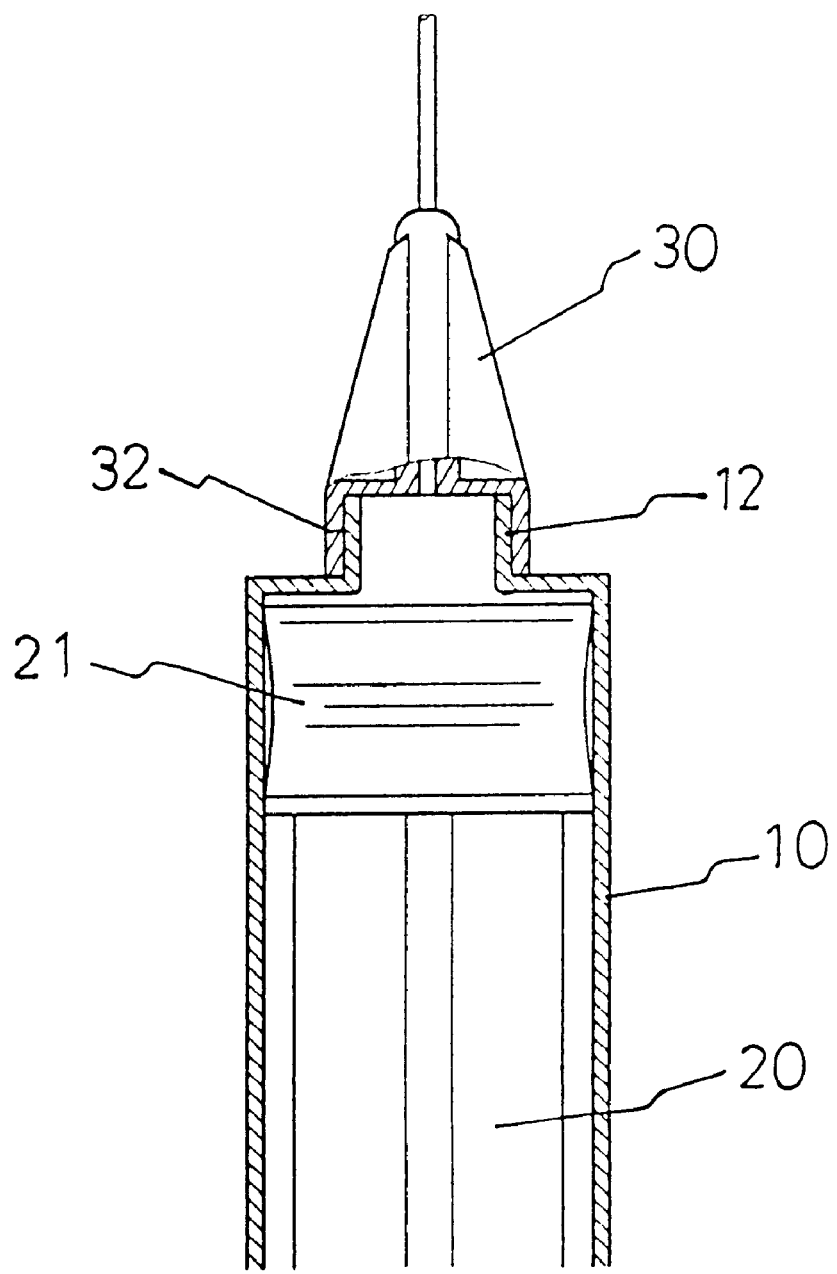
FIG. 2 is a sectional view of the prior art syringe.

For the purpose of promoting an understanding of the principles of the invention, reference will now be made to the embodiment illustrated in the drawings. Specific language will be used to describe the same. It will, nevertheless, be understood that no limitation of the scope of the invention is thereby intended, such alterations and further modifications in the illustrated device, and such further applications of the principles of the invention as illustrated herein being contemplated as would normally occur to one skilled in the art to which the invention relates.

Figure 3:
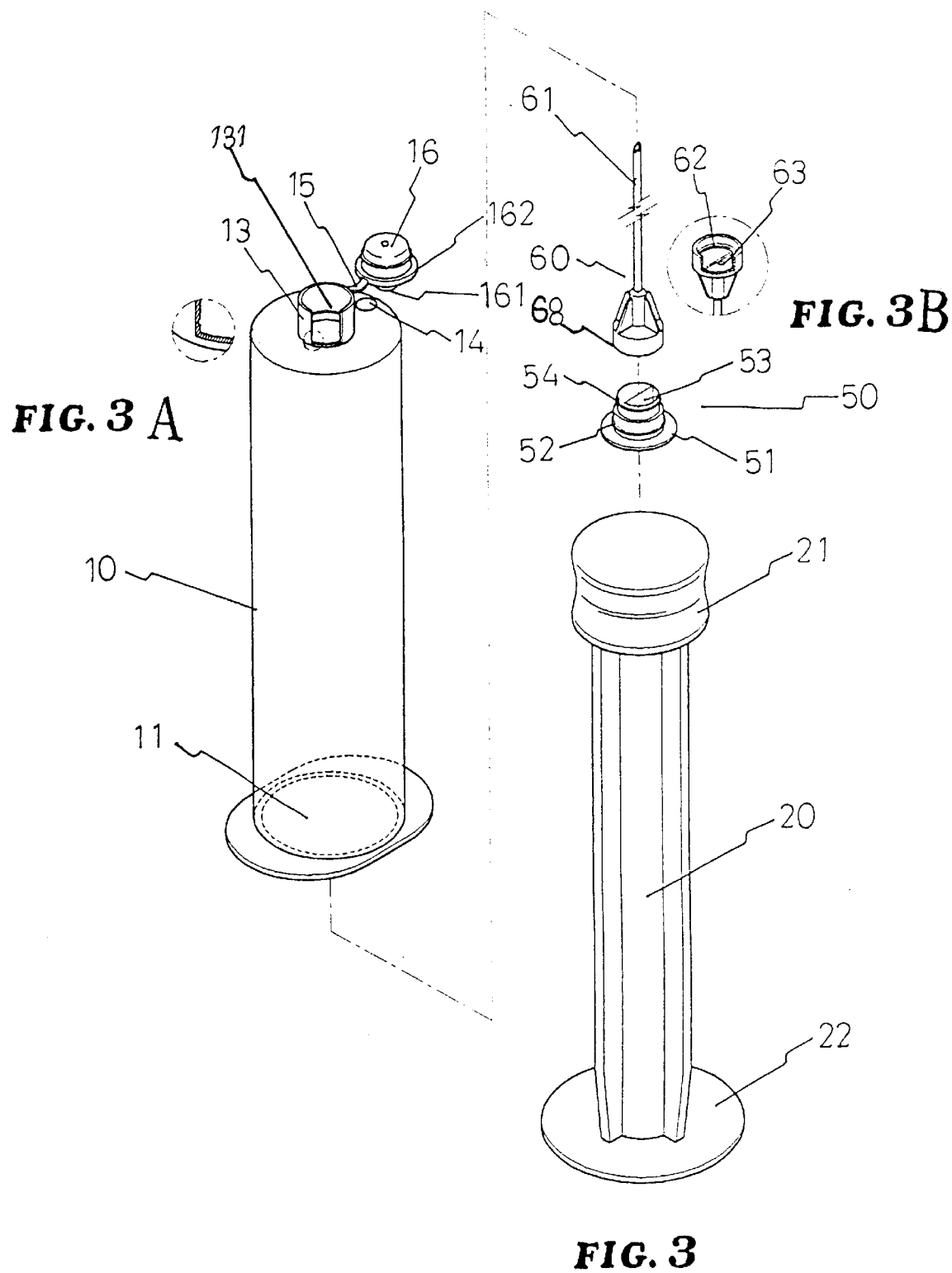
FIG. 3 is an exploded view of a safety syringe according to the present invention.
Figure 4:
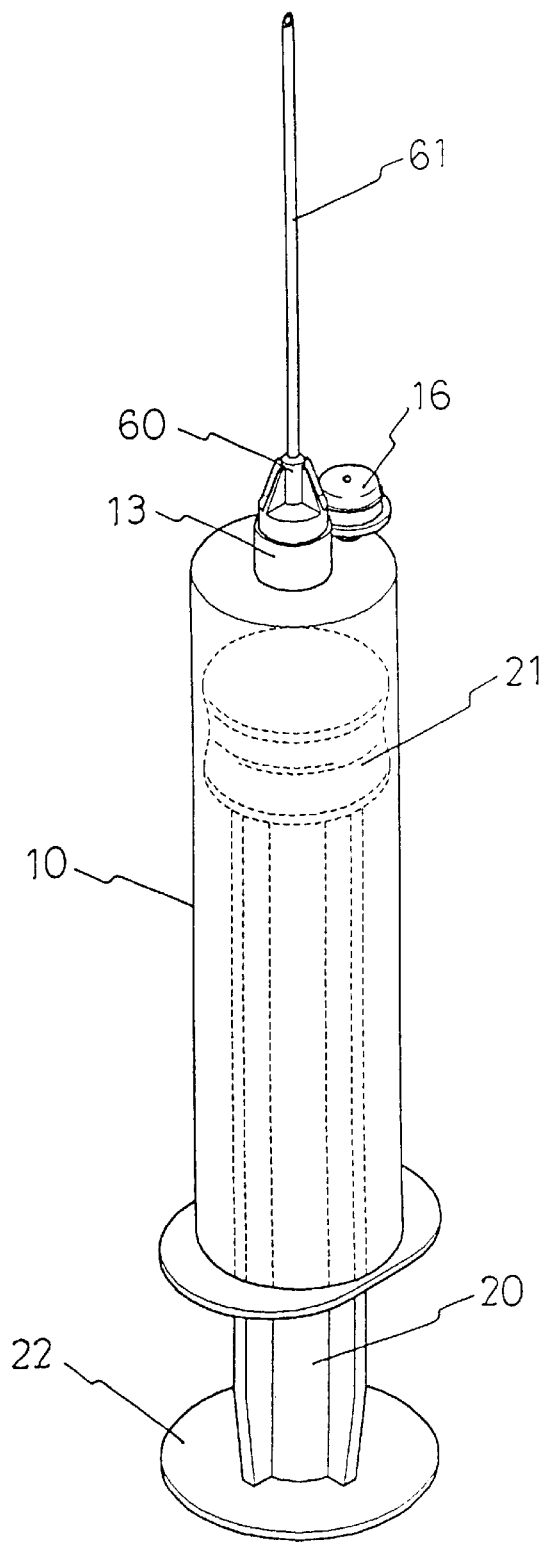
FIG. 4 is a perspective view of the safety syringe.
Figure 5:
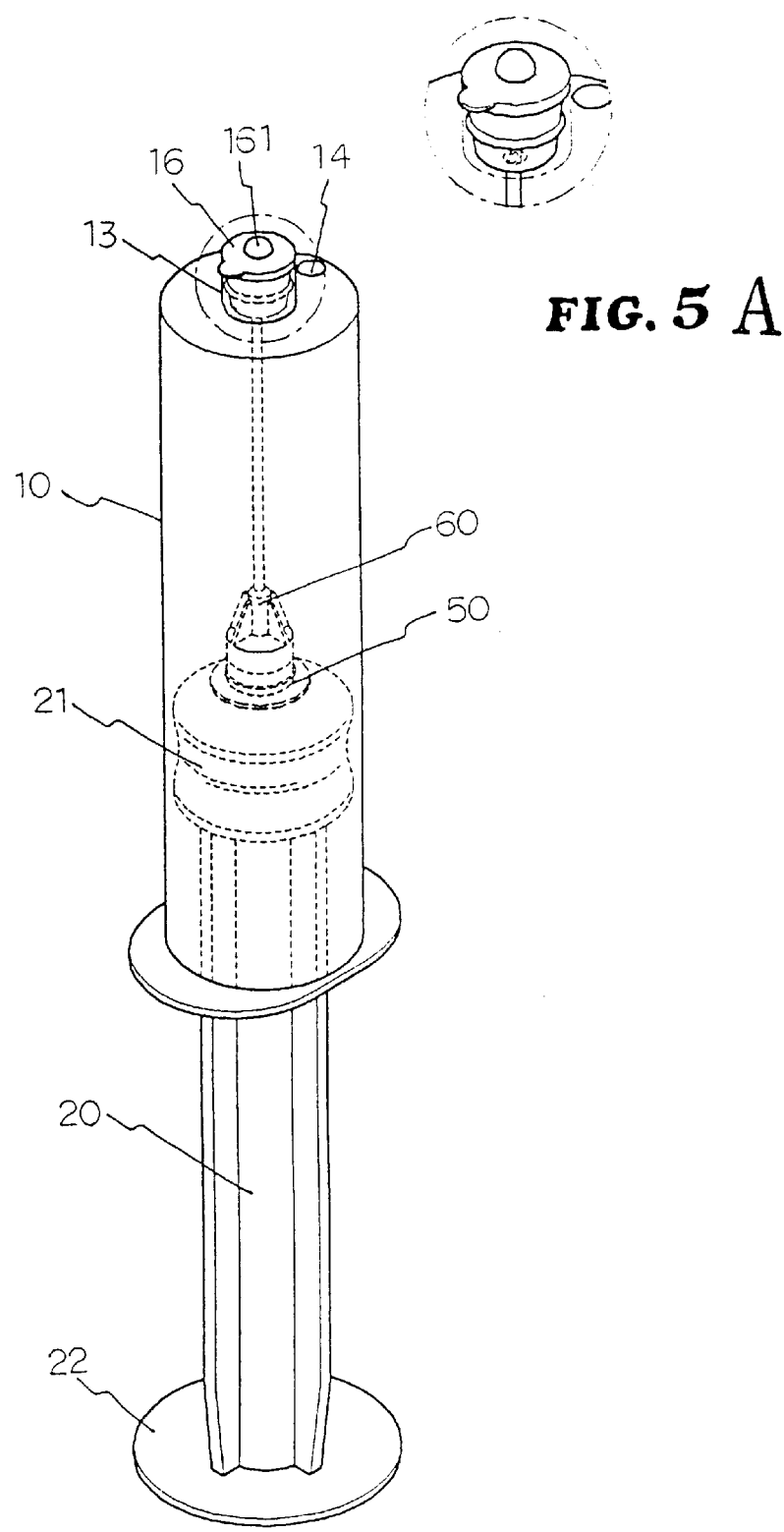
FIG. 5 is a perspective view of the safety syringe with the needle fitted inside the barrel.

With reference to the drawings and in particular to FIGS. 3 and 4 thereof, the safety syringe according to the present invention generally comprises a barrel 10, a plunger 20, a connector 50, and a needle 60.

The barrel 10 is a tubular member formed with an opening 11 at the bottom and a neck portion 13 at the top (with respect to FIG. 3). The neck portion 13 is of a smaller diameter with the other portion of the barrel 10. The top is formed with a cavity 14. The neck portion 13 has a flexible strap 15 connected to a cover 16 configured to fit into the neck portion 13. The cover 16 is provided with a protuberance 161 engageable with the cavity 14 and a flange 162 for sealing the neck portion 13. The interior of the neck portion 13 is formed with an annular groove 131. The inner top of the barrel 10 has an annular recess 17 concentric with the neck portion 13.

The plunger 20 is an elongated member configured to be slidably fitted in the barrel 10. The plunger 20 is provided with a rubber piston 21 at the upper end and a thumb plate 22 at the lower end.

The connector 50 is a cylindrical member formed with a flange 51 at the bottom, a first annular projection 52 above the flange 51, and a second annular projection 54 above the first annular projection 52. The connector 50 is fitted into the neck portion 13 of the barrel 10, with the flange 51 received in the annular recess 17 and the first annular projection 52 engaged with the annular groove 54. The connector 50 is formed with a semi-cylindrical vertical passage 53.

The needle 60 includes a tubular pin 61 and a conical base 68 at the lower end of the tubular pin 61. The conical base 68 is formed with a semi-cylindrical vertical passage 63 and an annular groove 62 at its inner side (see FIGS. 3 and 3A). The connector 50 is snugly-fitted into the conical base 68 of the needle 60, with the second annular projection 54 engaged with the annular groove 62, so that the conical base 68 can be rotated with respect to the connector 50 so as to make the semi-cylindrical vertical passage 63 align with the semi-cylindrical vertical passage 53 as desired.

In assembly, the connector 50 is put inside the barrel 10 and pushed upwardly to engage the flange 51 and first annular projection 52 of the former with the annular recess 17 and annular groove 131 of the latter. The base 68 of the needle 60 is force-fitted on the connector 50, with the annular groove 62 receiving the second annular projection 54 of the connector 50, so that the needle 60 can be rotated with respect to the connector 50 to align the semi-cylindrical vertical passage 63 with the semi-cylindrical vertical passage 53 as desired.

Figure 6:
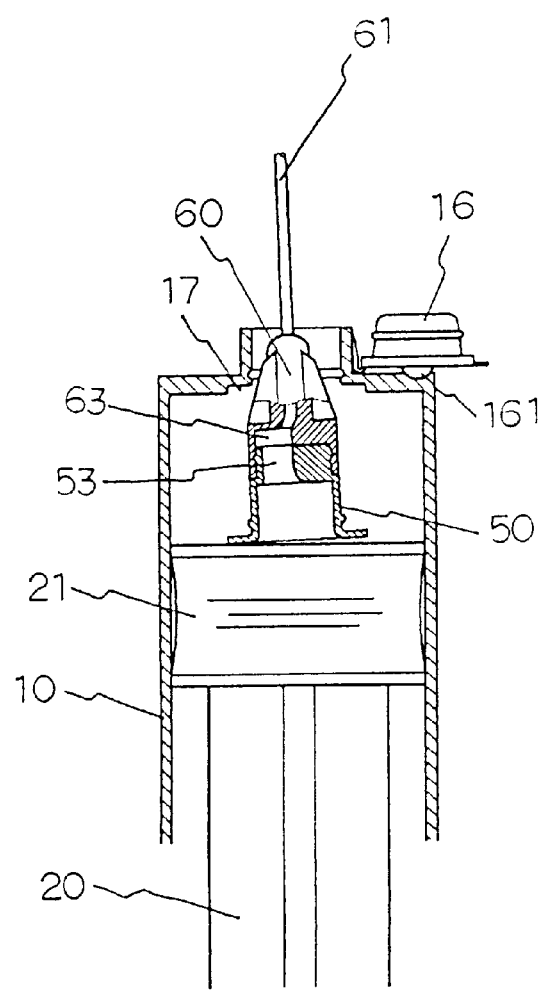
FIGS. 6A and 6B are sectional views illustrating how the safety syringe is used.
Figure 6:
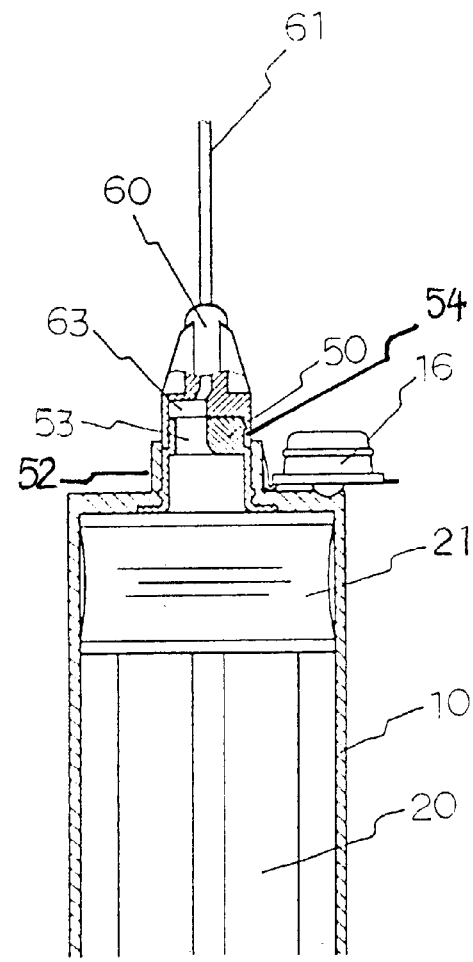

Before use, the needle 60 is rotated with respect to the connector 50, so that the semi-cylindrical vertical passage 63 is aligned with the semi-cylindrical vertical passage 53. When in use, the cover 16 is opened and the protuberance 161 of the cover 16 is snugly-fitted in the cavity 14 of the barrel 10. Thereafter, the plunger 20 is pushed into the barrel 10 so as to force the connector 50 to engage with the neck portion 13 and then pulled backward to draw liquid medicine (not shown) into the barrel 10 through the needle 60 (see FIGS. 6A and 6B).

After use, the needle 60 is turned through an angle of 180 degrees so that the semi-cylindrical vertical passage 63 is no longer in alignment with the semi-cylindrical vertical passage 53, and then the plunger 20 is pulled backward thereby generating vacuum inside the barrel 10 and therefore drawing the connector 50 together with the needle 60 into the barrel 10 (see FIGS. 7A and 7B). Thereafter, the neck portion 13 of the barrel is closed with the cover 16 to keep the needle 10 inside the barrel 10 thus avoiding accident sticks.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

I claim:

1. A safety syringe comprising:

a tubular barrel having a bottom formed with an opening and a top formed with a neck portion, said top being formed with a cavity, said neck portion having a flexible strap connected to a cover configured to fit into said neck portion, said cover being provided with a protuberance engageable with said cavity and a flange for sealing said neck portion, an interior of said neck portion being formed with a first annular groove, an inner top of said barrel having an annular recess concentric with said neck portion;

a plunger configured to be slidably fitted in said barrel and provided with a rubber piston at an inner end thereof and a thumb plate at an outer end thereof;

a cylindrical connector having a bottom formed with a flange, a first annular projection above said flange, and a second annular projection above said first annular projection, said connector being fitted into said neck portion with said flange received in said annular recess and said first annular projection engaged with said annular groove, said connector being formed with a first semi-cylindrical vertical passage; and a needle including a tubular pin and a conical base at a lower end of said tubular pin, said conical base being formed with a second semi-cylindrical vertical passage and a second annular groove at an inner side thereof, said conical base being rotatably engaged with said connector with said second annular projection engaged with said second annular groove.

* * * * *